US006818205B2

(12) United States Patent
Reinehr et al.

(10) Patent No.: US 6,818,205 B2
(45) Date of Patent: Nov. 16, 2004

(54) USE OF FLUORESCENT WHITENING AGENTS

(75) Inventors: Dieter Reinehr, Kandern (DE); Helmut Luther, Grenzach-Wyhlen (DE); Georges Metzger, Moernach (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 149 days.

(21) Appl. No.: 10/149,396

(22) PCT Filed: Dec. 7, 2000

(86) PCT No.: PCT/EP00/12342

§ 371 (c)(1),
(2), (4) Date: Jun. 11, 2002

(87) PCT Pub. No.: WO01/43714

PCT Pub. Date: Jun. 21, 2001

(65) Prior Publication Data

US 2003/0103924 A1 Jun. 5, 2003

(30) Foreign Application Priority Data

Dec. 13, 1999 (EP) ............................. 99811154

(51) Int. Cl.$^7$ ............................. A61K 7/42; A61K 7/44; A61K 7/00
(52) U.S. Cl. ............................. 424/59; 424/60; 424/400; 424/401
(58) Field of Search ............................. 424/59, 60, 400, 424/401

(56) References Cited

U.S. PATENT DOCUMENTS 6,313,181 B1 * 11/2001 Cohen ........................ 424/59

FOREIGN PATENT DOCUMENTS

| EP | 0742281 | 11/1996 |
| WO | 99/13822 | 3/1999 |

* cited by examiner

Primary Examiner—Shelley A. Dodson
(74) Attorney, Agent, or Firm—Kevin T. Mansfield

(57) ABSTRACT

The use of a polymeric carrier material treated with a fluorescent whitening agent, for lightening human skin and for protecting human skin against UV radiation, is described.

15 Claims, No Drawings

USE OF FLUORESCENT WHITENING AGENTS

The present invention relates to the use of a polymeric carrier material treated with a fluorescent whitening agent, for lightening human skin and for protecting human skin against UV radiation.

Melanin is a dark pigment that is found in the hair, the eyes and, especially, the skin, and that is formed in the so-called melanocytes by the conversion of the amino acid tyrosine in the presence of the enzyme tyrosinase. The number of melanocytes varies widely according to individual skin type.

Frequently, local areas of skin are to be found that have an increased melanin density. In such areas the number of melanocytes is significantly elevated, resulting in a skin colour that is far darker than the colour of the rest of the skin. Such local, hyperpigmented areas are known as brown spots, age spots or liver spots.

Women who have borne children and/or have taken the contraceptive pill for a prolonged period are frequently more especially subject to such spot formation. This undesired colour change is considered in particular by many women to be a disfigurement, and frequently leads to serious emotional disorders. Also, in many cultures in which parts of the population are coloured, especially in the Asiatic region, a naturally dark skin type that has elevated melanin concentration is undesirable. In regions such as those, depigmentation compositions are preferably used to lighten the skin.

In the past a number of topical preparations have been proposed for the prevention of hyperpigmentation that comprise one or more components, so-called depigmentation agents or bleaching agents, e.g. hydroquinone, hydroquinone derivatives, hydrocortisone and retinic acid, benzyloxyphenol (U.S. Pat. No. 3,060,097) or methoxyphenol. Such components bring about depigmentation by the oxidation or reduction of melanin, but a disadvantage of those active ingredients is that they may cause undesired skin reactions, or satisfactory formulation thereof into cosmetic preparations is not possible.

The problem of the present invention is to make available skin-lightening compositions that on the one hand have the effect of lightening the skin and that on the other hand are well tolerated by the skin and can be formulated cosmetically.

Surprisingly, it has now been found that a polymeric carrier material treated with a fluorescent whitening agent meets those requirements. In addition, such a material protects the human skin from the damaging effect of UV rays.

The present invention accordingly relates to the use of a polymeric carrier material treated with a fluorescent whitening agent for lightening human skin and for protecting human skin against UV radiation.

Preferred fluorescent whitening agents that can be used in accordance with the invention correspond to the formula

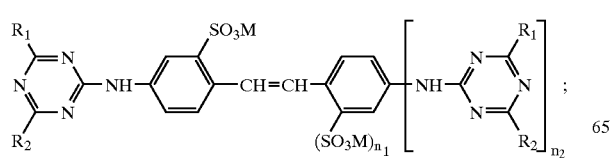
(1)

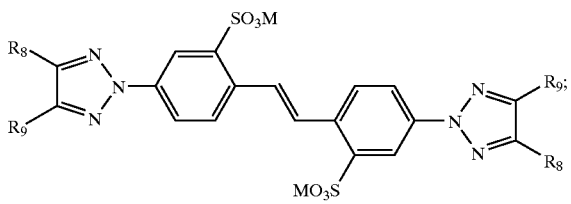
(2)

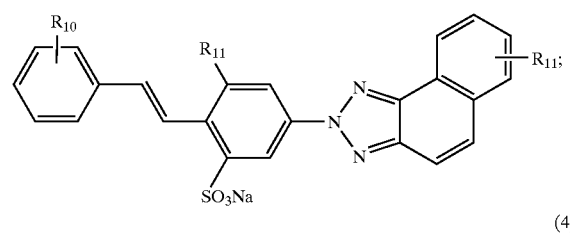
(3)

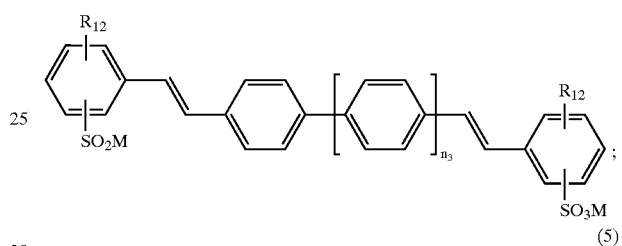
(4)

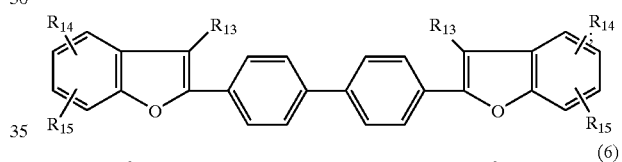
(5)

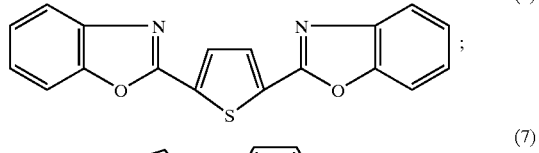
(6)

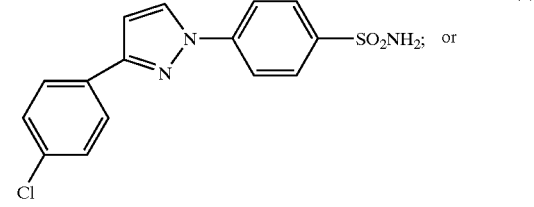
(7)

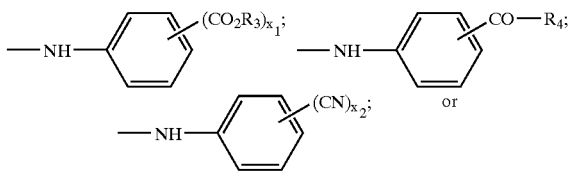
(8)

wherein $R_1$ is a radical of formula

-continued

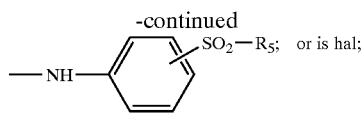

$R_3$ is M; unsubstituted or substituted alkyl or unsubstituted or substituted aryl;

$R_4$ is hydrogen; unsubstituted or substituted alkyl or unsubstituted or substituted aryl; or —$NR_6R_7$, wherein $R_6$ and $R_7$ are each independently of the other hydrogen; unsubstituted or substituted alkyl or unsubstituted or substituted aryl; or $R_6$ and $R_7$ together with the nitrogen atom binding them form a heterocyclic radical, especially a morpholino or piperidino radical, $R_5$ is hydrogen, unsubstituted or substituted alkyl or unsubstituted or substituted aryl, or a radical of formula (1a)
—$(CH_2)_{x_2}$—O—$SO_3$—M;

$R_2$ is hydrogen, unsubstituted or substituted alkyl or unsubstituted or substituted aryl; or a radical of formula

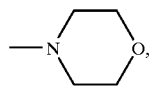

—OH, —$NH_2$, —$N(OH_2OH_2OH)_2$; —$N[CH_2CH(OH)CH_3]_2$; —NH—$R_3$; —$N(R_3)_2$ or —$OR_3$; or $R_1$ and $R_2$ are each independently of the other —OH, —Cl; —$NH_2$, —O—$C_1$–$C_4$alkyl, —O—aryl, —NH—$C_1$–$C_4$alkyl, —$N(C_1$–$C_4$alkyl$)_2$, —$N(C_1$–$C_4$alkyl), —N(hydroxy-$C_1$–$C_4$alkyl), —N(hydroxy-$C_1$–$C_4$alkyl$)_2$; —NH-aryl, morpholino; or S—$C_1$–$C_4$alkyl(aryl);

$R_8$ and $R_9$ are each independently of the other hydrogen, $C_1$–$C_4$alkyl, phenyl or a radical of formula

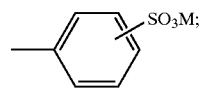

$R_{10}$ is hydrogen, Cl or $SO_3M$;
$R_{11}$ is —CN, —$SO_3M$, —$S(C_1$–$C_4$alkyl$)_2$ or $S(aryl)_2$;
$R_{12}$ is hydrogen, —$SO_3M$, —O—$C_1$–$C_4$alkyl, —CN, —Cl, —COO—$C_1$–$C_4$alkyl or $CON(C_1$–$C_4$alkyl$)_2$;
$R_{13}$ is hydrogen; —$C_1$–$C_4$alkyl, —Cl or —$SO_3M$;
$R_{14}$ and $R_{15}$ are each independently of the other hydrogen, $C_1$–$C_4$alkyl, —$SO_3M$, —Cl or —O—$C_1$–$C_4$alkyl;
$R_{16}$ is hydrogen or $C_1$–$C_4$alkyl;
$R_{17}$ is hydrogen, $C_1$–$C_4$alkyl, —CN, —Cl, —COO—$C_1$–$C_4$alkyl, —CON ($C_1$–$C_4$alkyl$)_2$, aryl or —O-aryl;
M is hydrogen, Na, K, Ca, Mg, ammonium, mono-, di-, tri- or tetra-$C_1$–$C_4$alkylammonium, mono-, di- or tri-$C_1$–$C_4$hydroxyalkylammonium, or ammonium di- or tri-substituted by a mixture of $C_1$–$C_4$alkyl and $C_1$–$C_4$hydroxyalkyl groups;
$n_1$, $n_2$ and $n_3$ are each independently of the others 0 or 1;
$x_1$ is 1 or 2; and
$x_2$ is from 1 to 3.

$R_2$, $R_3$, $R_4$, $R_5$, $R_6$ and $R_7$ in the meaning of (unsubstituted or) substituted alkyl is $C_1$–$C_{12}$alkyl, preferably $C_1$–$C_4$alkyl. The alkyl groups may be branched or unbranched and may be unsubstituted or substituted by halogen, e.g. fluorine, chlorine or bromine, by $C_1$–$C_4$alkoxy, e.g. methoxy or ethoxy, by phenyl or carboxyl, by $C_1$–$C_4$alkoxycarbonyl, e.g. acetyl, by mono- or di-$C_1$–$C_4$alkylamino or by —$SO_3M$.

$R_2$, $R_3$, $R_4$, $R_5$, $R_6$ and $R_7$ in the meaning of (unsubstituted or) substituted aryl is preferably a phenyl or naphthyl group that may be unsubstituted or substituted by $C_1$–$C_4$alkyl, e.g. methyl, ethyl, propyl, isopropyl, butyl, isobutyl, sec-butyl or tert-butyl, by $C_1$–$C_4$alkoxy, e.g. methoxy, ethoxy, propoxy, isopropoxy, butoxy, isobutoxy, sec-butoxy or tert-butoxy, by halogen, e.g. fluorine, chlorine or bromine, by $C_2$–$C_5$alkanoylamino, e.g. acetylamino, propionylamino or butyrylamino, by nitro, by sulfo or by di-$C_1$–$C_4$alkylated amino.

The compounds of formula (1) are preferably used in neutral form, that is to say M is preferably a cation of an alkali metal, especially sodium, or an amine.

In the compounds of formula (1), $R_1$ is preferably a radical of formula

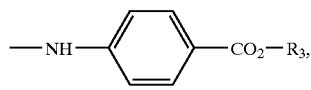

wherein $R_3$ has the meanings given above and is preferably $C_1$–$C_4$alkyl, especially methyl or ethyl; or a radical of formula

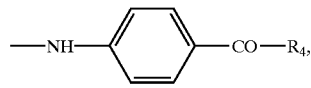

wherein $R_4$ has the meanings given above and is preferably $C_1$–$C_4$alkyl, especially methyl or ethyl, or —$NR_6R_7$, wherein $R_6$ and $R_7$ have the meanings given above and are preferably hydrogen, $C_1$–$C_4$alkyl, especially methyl or ethyl, a morpholino or piperidino radical, more especially hydrogen, or a radical of formula

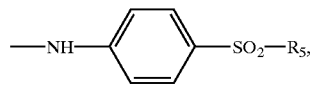

wherein $R_5$ has the meanings given above and is preferably $C_1$–$C_4$alkyl substituted by —$SO_3M$, especially methyl or ethyl substituted by —$SO_3M$, wherein M has the meanings given above and Is preferably sodium; and $R_2$ is preferably

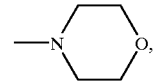

—$NH_2$, —$N(CH_2CH_2OH)_2$ of —$N[CH_2CH(OH)CH_3]_2$.

The compounds of formula (1) can be prepared under known reaction conditions by the reaction of cyanuric chloride with the corresponding aminostilbenesulfonic acids and with an amino compound that is capable of introducing a group $R_1$ and with a compound that is capable of introducing a group $R_2$, $R_1$ and $R_2$ having the meanings given above.

The fluorescent whitening agents that can be used with advantage in the present invention are listed by way of example in the following Table 1:

TABLE 1
| Compound of formula | |
|---|---|
| (9) | 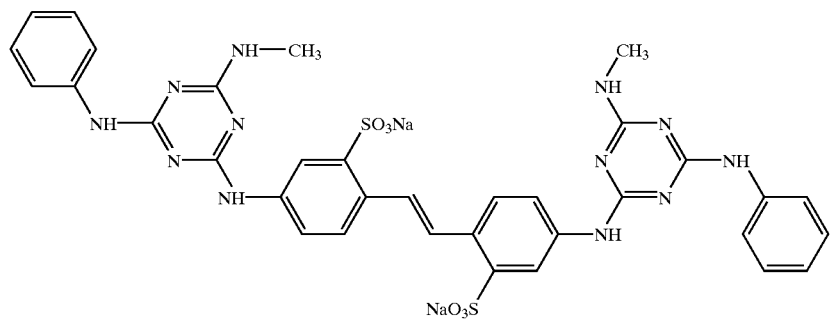 |
| (10) | 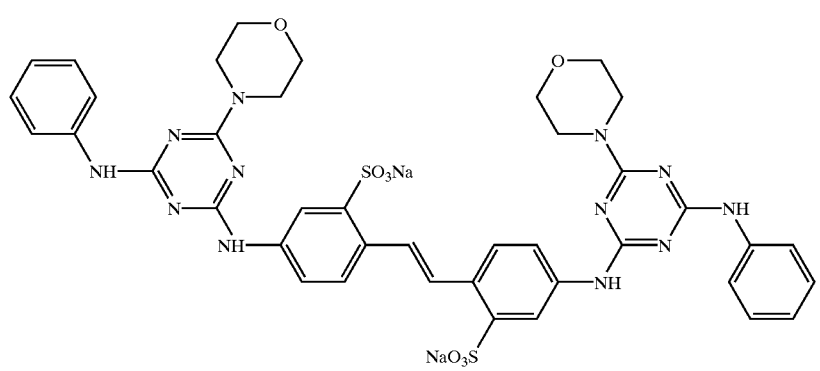 |
| (11) | 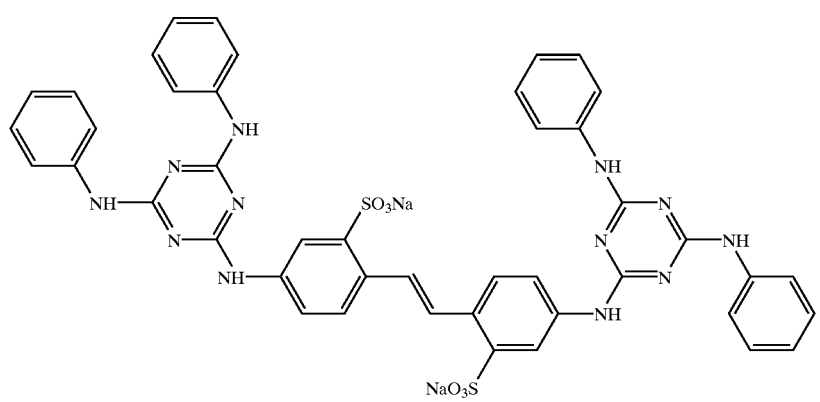 |
| (12) | 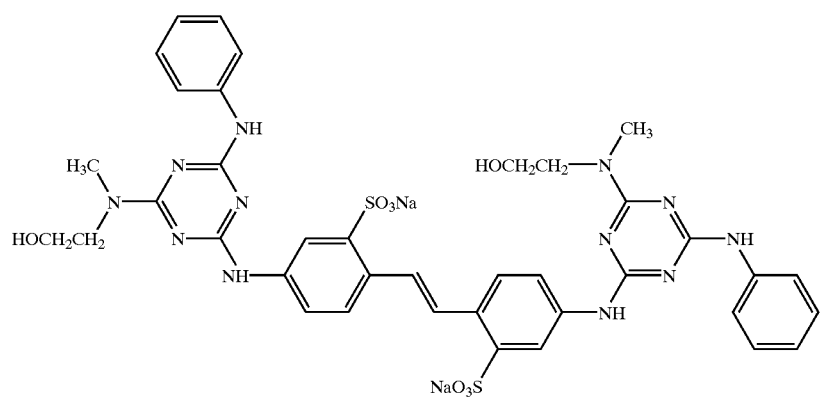 |

TABLE 1-continued
Compound of formula
(13) 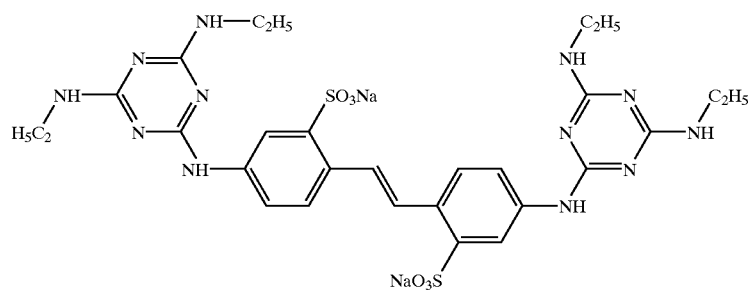
(14) 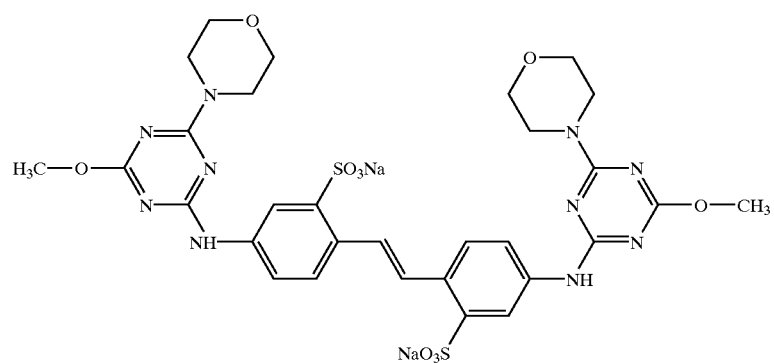
(15) 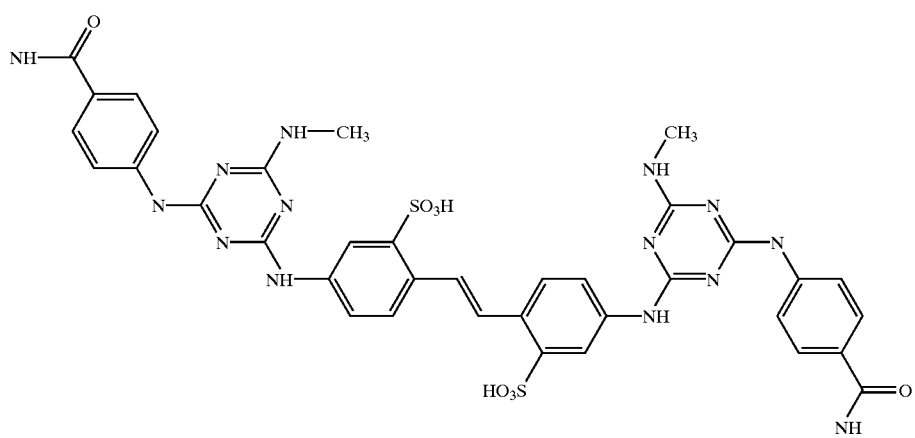
(16) 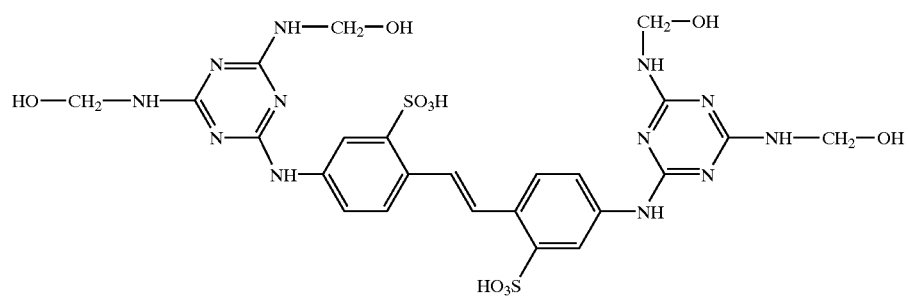

TABLE 1-continued
| Compound of formula | |
|---|---|
| (17) | 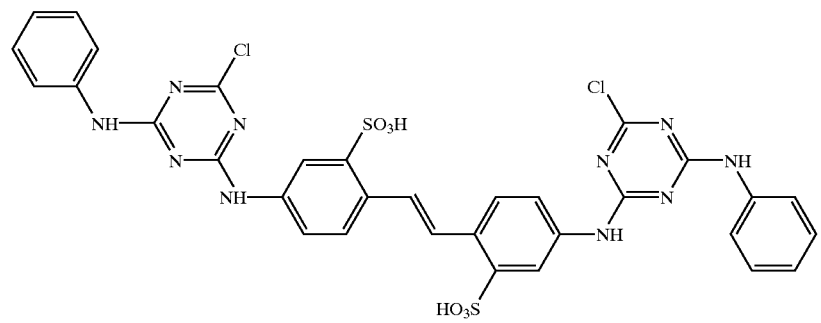 |
| (18) | 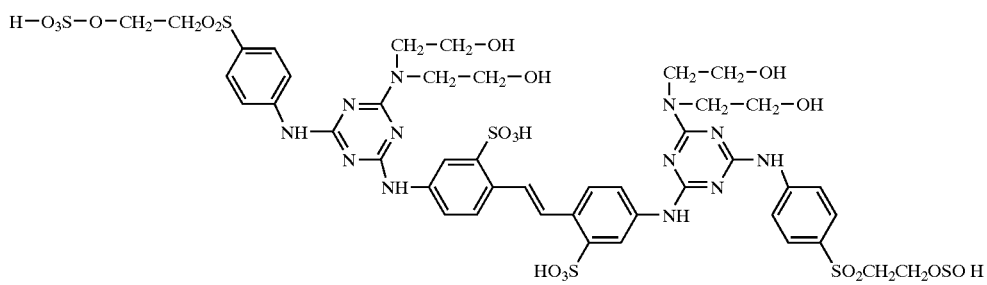 |
| (19) | 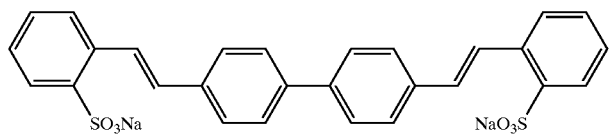 |
| (20) | 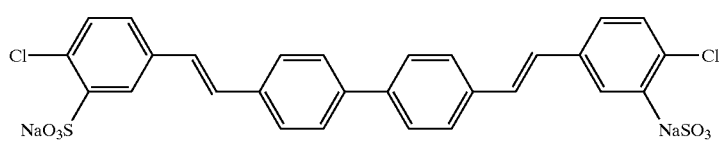 |
| (21) | 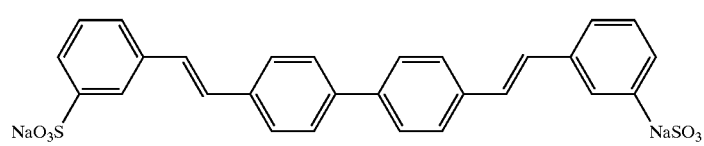 |
| (22) | 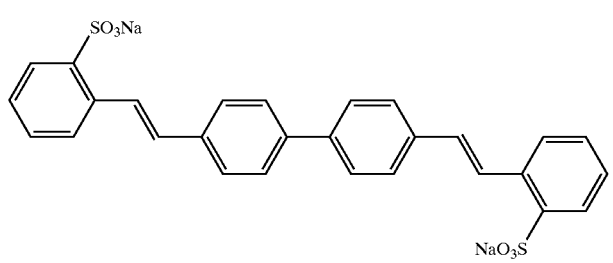 |

TABLE 1-continued
Compound of formula
(23) 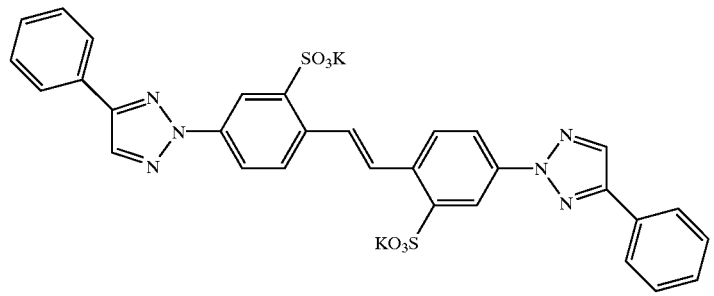
(24) 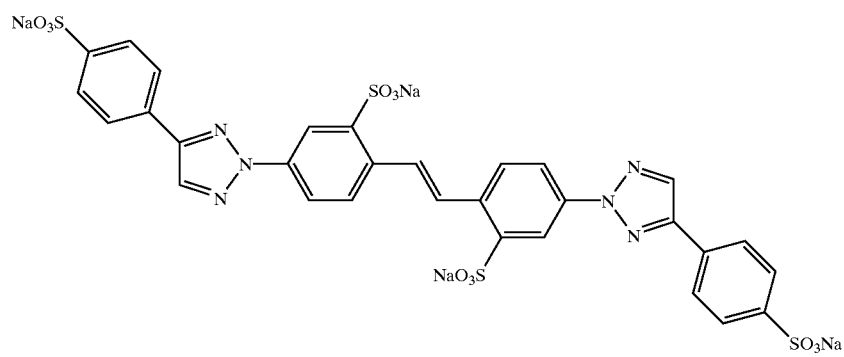
(25) 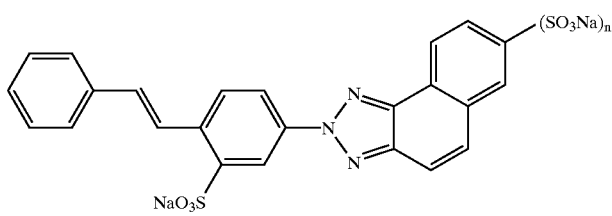
(26) 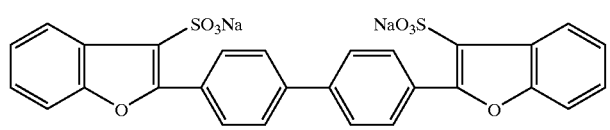
(27) 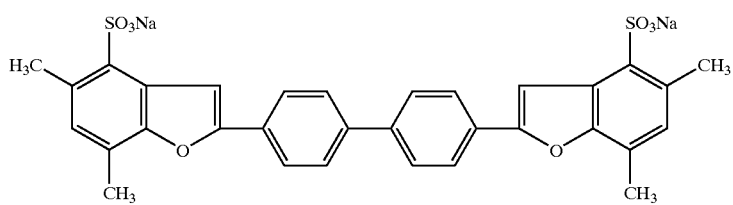
(28) 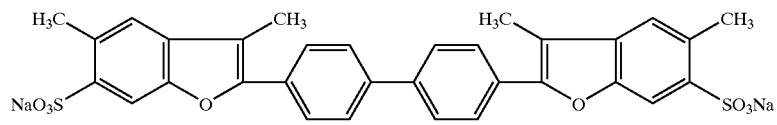
(29) 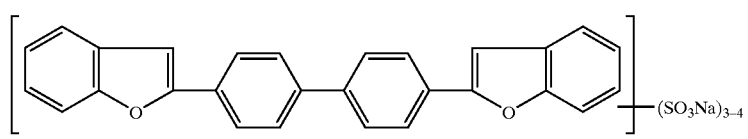

TABLE 1-continued

Compound of formula (30)

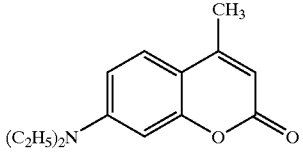

In principle, as polymeric carriers for use in accordance with the invention there come into consideration materials that are suitable for cosmetic or pharmaceutical preparations. The polymeric materials may be of natural origin or are obtainable synthetically, e.g. starch, starch derivatives, e.g. hydroxypropyl-distarch phosphate, polyvinylpyrrolidones, polyvinyl-polypyrrolidones, polyacrylates, acrylates/steareth-20, methacrylate copolymers, acrylate copolymers, acrylate-octylpropenamide copolymer (Dermacryl 79), acrylate/vinyl isodecanoate cross polymer, $C_{1-10}$polycarbamyl-polyglycol esters; $C_1$–$C_{18}$polycarbamyl-polyglycol esters, acrylate/hydroxy ester acrylate copolymer, acrylate-octylacrylamide; polyacrylamide: polyamides, polyvinylcaprolactam, polyvinyl alcohols, polyolefin dispersions, polyesters, sodium polystyrenesulfonates, latex particles (of all kinds of polymers and copolymers), chitosan and derivatives, xanthans, Gellan, hyaluronic acid, cellulose, cellulose ethers, polyglucans, CM-glucans, alginates, hydroxyethyl cellulose, hydroxypropyl cellulose, cyclodextrins ($\alpha$-, $\beta$-, $\gamma$-) and their derivatives, polyoxyethylene-polyoxypropylene block polymers, (hydrolysed) collagen, (hydrolysed) elastin, (hydrolysed) keratin, collagen, gelatin, gum arabic and polyquarternium-X (1-10).

The polymeric material preferably used is cellulose.

To prepare a polymeric carrier material treated with a fluorescent whitening agent, the above-mentioned fluorescent whitening agents can be applied to an appropriate carrier. This can be carried out by mixing the carrier materials with the appropriate fluorescent whitening agent in a suitable solvent. When, for example, a solvent in which the fluorescent whitening agent is soluble but the polymeric carrier material is insoluble is used, the dissolved fluorescent whitening agent can be applied directly to the polymeric carrier material. The solvent can be removed from the resulting treated polymeric carrier material by suitable physical separating methods.

When a solvent, e.g. water, in which the fluorescent whitening agent and the polymeric carrier material are soluble, or—in the case of the carrier material—swellable, is used, the entire whitening agent/polymeric carrier material/solvent mixture can be incorporated into an appropriate cosmetic or pharmaceutical formulation. It is, however, also possible to remove the solvent from the mixture by suitable methods before the mixture is used further.

The polymeric carrier materials treated with a fluorescent whitening agent can also be prepared by chemical reaction of the polymeric carrier material with the appropriate fluorescent whitening agent.

The polymeric carrier materials treated with a fluorescent whitening agent so obtained are suitable for lightening human skin. They simultaneously offer effective protection against UV radiation. A further advantage of such materials is that the actual active substance, that is the fluorescent whitening agent, does not come into direct contact with the skin.

For cosmetic and pharmaceutical use, the treated polymeric carrier materials can be incorporated into appropriate formulations.

The invention accordingly relates also to a cosmetic formulation that comprises a polymeric carrier material treated with a fluorescent whitening agent, as well as cosmetically tolerable carriers or adjuvants.

The cosmetic formulation may, in addition to containing the polymeric carrier material treated with a fluorescent whitening agent, also contain one or more further UV-protective substances from the following classes of substance:

1. p-aminobenzoic acid derivatives. e.g. 4-dimethylaminobenzoic acid 2-ethylhexyl ester;
2. salicylic acid derivatives, e.g. salicylic acid 2-ethylhexyl ester;
3. benzophenone derivatives, e.g. 2-hydroxy-4-methoxybenzophenone and the 5-sulfonic acid derivative thereof;
4. dibenzoylmethane derivatives, e.g. 1-(4-tert-butylphenyl)-3-(4-methoxyphenyl)propane-1,3-dione;
5. diphenyl acrylates, e.g. 2-ethylhexyl-2-cyano-3,3-diphenyl acrylate and 3-(benzofuranyl)-2-cyanoacrylate;
6. 3-imidazol-4-yl-acrylic acid and esters;
7. benzofuran derivatives, especially 2-(p-aminophenyl) benzofuran derivatives, described in EP-A-582 189, U.S. Pat. Nos. 5,338,539, 5,518,713 and EP-A-613 893;
8. polymeric UV absorbers, e.g. the benzylidene malonate derivatives described in EP-A-709 080;
9. cinnamic acid derivatives, e.g. the 4-methoxycinnamic acid 2-ethylhexyl ester and iso-amyl ester disclosed in U.S. Pat. No. 5,601,811 and WO 97/00851;
10. camphor derivatives, e.g. 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine-bis (7,7-dimethyl-2-oxo-bicyclo [2.2.1]heptane-1-methanesulfonic acid) and salts, 3-(4'-sulfo)benzylidene-bornan-2-one and salts;
11. trianilino-s-triazine derivatives, e.g. 2,4,6-trianilino-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;
12. 2-hydroxyphenyl-benzotriazole derivatives;
13. 2-phenylbenzimidazole-5-sulfonic acid and salts thereof;

14. menthyl-o-aminobenzoate;
15. $TiO_2$ (variously encapsulated), ZnO and mica;
16. hydroxyphenyltriazines, e.g. compounds of formula

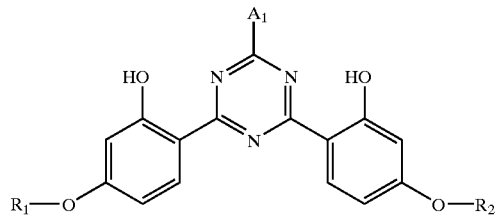
(31)

wherein $R_1$ and $R_2$ are each independently of the other $C_3$–$C_{18}$alkyl; $C_2$–$C_{18}$alkenyl; or a radical of formula —$CH_2$—CH(—OH)—$CH_2$—O—$T_1$; or
$R_1$ and $R_2$ are a radical of formula (31a)

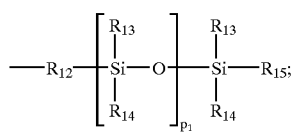

$R_{12}$ is a direct bond, a straight-chain or branched $C_1$–$C_4$alkylene radical or a radical of formula —$C_{m_1}H_{2m_1}$— or —$C_{m_1}H_{2m_1}$—O—;
$R_{13}$, $R_{14}$ and $R_{15}$ are each independently of the others $C_1$–$C_{18}$alkyl; $C_1$–$C_{18}$alkoxy or a radical of formula

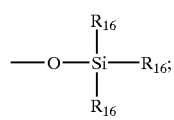

$R_{16}$ is $C_1$–$C_5$alkyl;
$m_1$ and $m_3$ are each independently of the other from 1 to 4;
$P_1$ is 0 or a number from 1 to 5;
$A_1$ is a radical of formula

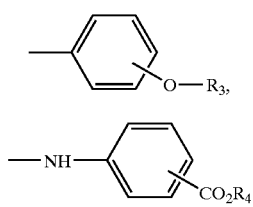
(31b)

(31c)

or of formula (31d)

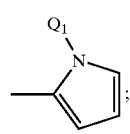

$R_3$ is hydrogen; $C_1$–$C_{10}$alkyl; —($CH_2CHR_5$—O)$_{n_1}$—$R_4$; or a radical of formula —$CH_2$—CH(—OH)—$CH_2$—O—$T_1$;
$R_4$ is hydrogen; M; $C_1$–$C_5$alkyl; or a radical of formula —($CH_2$)$_{m_2}$—O—$T_1$;

$R_5$ is hydrogen; or methyl;
$T_1$ is hydrogen; or $C_1$–$C_8$alkyl;
$Q_1$ is $C_1$–$C_{18}$alkyl;
M is a metal cation;
$m_2$ is from 1 to 4; and
$n_1$ is from 1 to 16;

especially the triazine compound of formula

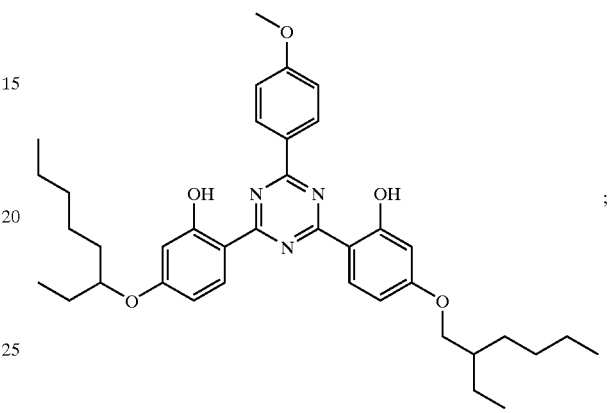
(31a)

17. micronised organic UV absorbers, especially compounds of formula

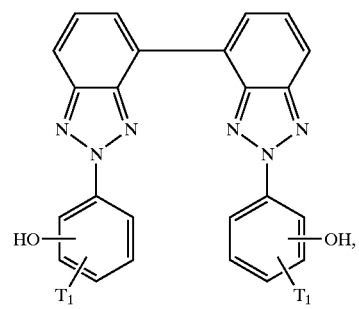
(32)

wherein $T_1$ is hydrogen; or $C_1$–$C_{12}$alkyl; more especially benzotriazole compounds of formula

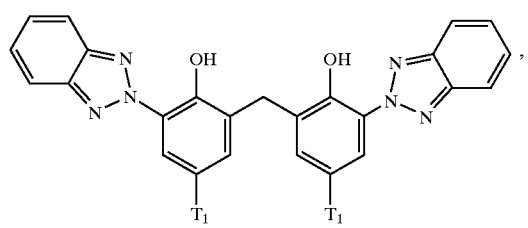
(32a)

wherein $T_1$ has the meanings given for formula (32) and is preferably methyl, tert-butyl or isooctyl.

Also, the UV absorbers described in "Sunscreens", Eds. N. J. Lowe, N. A. Shaath, Marcel Dekker, Inc., New York and Basle or in Cosmetics & Toiletries (107), 5off (1992) can be used as additional UV-protective substances in the formulation according to the invention.

The cosmetic or pharmaceutical formulation according to the invention can furthermore also be used together with known antioxidants, e.g. vitamin E, carotinoids or flavonoids.

The cosmetic formulation according to the invention contains from 0.1 to 15% by weight, preferably from 0.5 to 10% by weight, based on the total weight of the composition, of a polymeric carrier material treated with a fluorescent whitening agent, as well as a cosmetically tolerable adjuvant.

The cosmetic or pharmaceutical formulation can be prepared by physically mixing the treated polymeric carrier material with the adjuvant using customary methods, e.g. by simply stirring together the individual components.

The cosmetic formulation according to the invention may be formulated as a water-in-oil or oil-in-water emulsion, as an oil-in-alcohol lotion, as a vesicular dispersion of an ionic or non-ionic amphiphilic lipid, as a gel, cream or lotion, a solid stick, powder, make-up, foam, paste, suspension or stick, or as an aerosol formulation.

In the case of a water-in-oil or oil-in-water emulsion, the cosmetically/pharmaceutically tolerable adjuvant contains preferably from 5 to 50% of an oily phase, from 5 to 20% of an emulsifier and from 30 to 90% water. The oily phase may comprise any oil suitable for cosmetic/pharmaceutical formulations, e.g. one or more hydrocarbon oils, a wax, a natural oil, a silicone oil, a fatty acid ester or a fatty alcohol. Preferred mono- or poly-ols are ethanol, iso-propanol, propylene glycol, hexylene glycol, glycerol and sorbitol.

Any conventionally used emulsifier can be used for the cosmetic or pharmaceutical formulation according to the invention, e.g. one or more ethoxylated esters of natural derivatives, e.g. polyethoxylated esters of hydrogenated castor oil, or a silicone oil emulsifier, e.g. silicone polyol; a fatty acid soap which may or may not be ethoxylated; an ethoxylated fatty alcohol; a sorbitan ester which may or may not be ethoxylated; an ethoxylated fatty acid; or an ethoxylated glyceride.

The cosmetic or pharmaceutical formulation may also contain further components, e.g. emollients, emulsion stabilisers, skin humectants, thickeners, e.g. xanthan, moisture-retaining agents, e.g. glycerol, preservatives, perfumes and colourants.

The carrier materials treated with a fluorescent whitening agent that can be used in accordance with the invention are also suitable for improving the appearance of cosmetic or pharmaceutical formulations. Frequently, the intrinsic colour especially of cosmetic formulations is an undesirable beige, or is even yellowish, as a result of the intrinsic colour of the components. The use of a polymeric carrier material treated with a fluorescent whitening agent according to the invention allows the degree of whiteness of such formulations to be increased. At the same time, the UV-absorbing properties of those carrier materials provides such products and their components with effective protection against the damaging effect of UV radiation.

The invention relates also to the use of the carrier materials treated with a fluorescent whitening agent for improving the degree of whiteness of cosmetic or pharmaceutical formulations.

The following Examples serve to illustrate the present invention.

EXAMPLE 1

Fluorescent Whitening Agent Immobilised on a Starch Derivative 0.5 g of the fluorescent whitening agent of formula

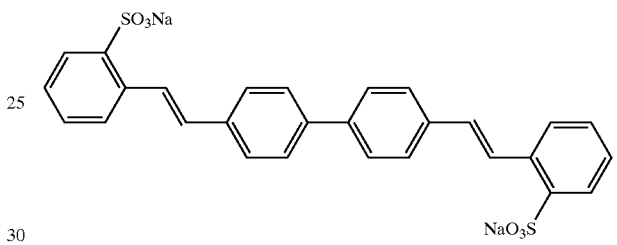

(101)

is dissolved in 100 g of water. 30 g of aluminum starch-octenyl succinate are added thereto and the batch is stirred at room temperature for approximately 15 min. The starch derivative is then filtered off and dried and is available for incorporation into formulations.

EXAMPLE 2

Fluorescent Whitening Agent Immobilised on an Acrylate/Tert-octylpropenamide Copolymer 0.15 g of the compound of formula

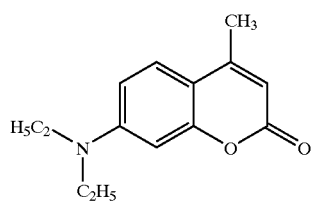

(102)

is dissolved in 100 g of ethanol. Acrylate/tert-octylpropenamide copolymer (Dermacryl 79. National Starch) is added thereto and the batch is stirred at room temperature for approximately 15 min. The polymer endowed with the fluorescent whitening agent is then precipitated by the addition of water, filtered off and dried.

EXAMPLE 3

Fluorescent Whitening Agent Immobilised on Starch 0.3 g of the fluorescent whitening agent of formula

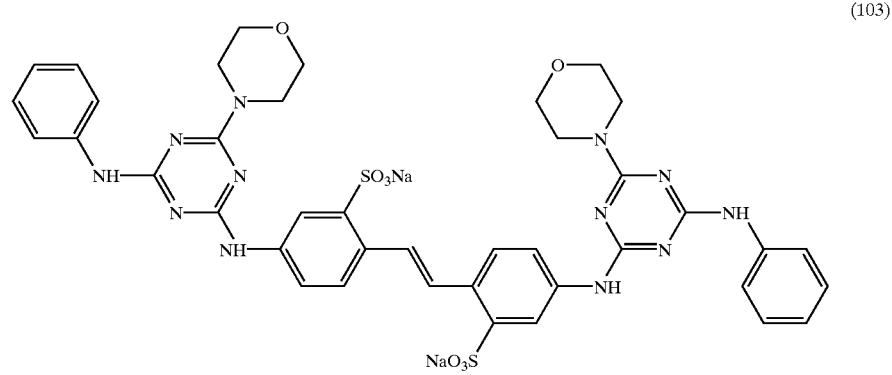

(103)

is dissolved in 100 g of water. Starch powder is added thereto and the batch is stirred at room temperature for approximately 15 min. The starch endowed with the fluorescent whitening agent is then filtered off and dried.

EXAMPLE 4

Preparation of a Sun-protection Cream

|  |  | % w/w |
|---|---|---|
| Phase (A) | octyl methoxycinnamate | 7.50 |
|  | PEG 40 stearate | 1.00 |
|  | glyceryl stearate SE | 2.00 |
|  | cetyl alcohol | 1.00 |
|  | $C_{12}$–$C_{15}$alkylbenzoates | 5.00 |
|  | cyclomethicone | 3.00 |
|  | phenyltrimethicone | 1.00 |
|  | dimethicone copolyol | 1.00 |

-continued

|  |  | % w/w |
|---|---|---|
| Phase (B) | deionised water | ad 100 |
|  | triethanolamine | 4.00 |
|  | compound of formula (101) | 1.00 |
|  | 2-phenylbenzimidazole-5-sulfonic acid | 4.00 |
|  | preservative | 0.5% |
|  | carbomer 940 (2% aqueous solution) | 25.00 |
| Phase (C) | propylene glycol | 3.00 |
|  | aluminium-starch-octenyl succinate | 3.00 |

With stirring at 80° C., phase (A) is introduced into phase B and the batch is homogenised.
Phase (C) (slurry) is added thereto at 40° C. while stirring well and the batch is allowed to cool, with stirring.
On being applied thinly, the cream lightens the skin significantly.

EXAMPLE 5

Preparation of an O/W Sun-protection Lotion

|  |  | % w/w |
|---|---|---|
| Phase (A) | polyglyceryl-3-methylglucose distearate | 2.0 |
|  | decyl oleate | 5.7 |
|  | isopropyl palmitate | 5.0 |
|  | caprylic/capric triglyceride | 6.5 |
|  | compound of formula (31a) | 2.0 |
|  | octylmethoxycinnamate | 5.0 |
| Phase (B) | glycerol | 3.0 |
|  | Phenonip | 0.5 |
|  | water | ad 100 |
| Phase (C) | carbomer 141 + 0.002 g of compound of formula (101) | 0.2 |
|  | isopropyl palmitate | 0.8 |

-continued

| | | % w/w |
|---|---|---|
| Phase (D) | micronised UV absorber of formula (104) | 4.0 |

[Chemical structure of a bis-benzotriazole phenol compound with tert-octyl substituents]

| Phase (E) | NaOH (10%) | as required |
|---|---|---|

Phases (A) and (B) are separately heated to 80° C. and combined without stirring. After the addition of (C), the batch is intensively homogenised. With gentle stirring, the batch is cooled to room temperature. The compound of formula (104) (D), adjusted to pH 5.5 using citric acid (20% solution), is added in portions with careful stirring. For the purpose of thorough mixing, the batch is then stirred for a further 15 min.. Finally, the desired final pH value is set using (E).
On direct comparison with an emulsion without immobilised whitening agent, the so-prepared emulsion can clearly be distinguished as lighter ("whiter"), the slight yellowish colouration of the placebo formulation disappearing.

EXAMPLE 6

Preparation of a W/O Sun-protection Emulsion

| | | % w/w |
|---|---|---|
| (A) | polyglyceryl-2-dipolyhydroxystearate | 3 |
| | glyceryl oleate | 1 |
| | caprylic/capric triglycerides | 6 |
| | octyl dodecanol | 6 |
| | Cetearyl isononanoate | 5 |
| | tocopheryl acetate | 1 |
| | fluorescent whitening agent of formula (102) | 2 |
| | cera alba | 1.2 |
| (B) | water | ad 100 |
| | micronised UV absorber of formula (104) | 10 |
| | glycerol 86% | 5 |
| | Phenonip | 0.5 |

Phases (A) and (B) are separately heated to 75° C. With stirring, phase (B) is slowly added to phase (A) and the batch is slowly cooled down to 40° C. After brief intensive homogenisation, the batch is allowed to cool to room temperature with stirring.

EXAMPLE 7

Preparation of a Lotion

| | | % w/w |
|---|---|---|
| Phase (A) | cetyl alcohol | 1.00% |
| | glyceryl stearate | 1.00 |
| | ceteth 10 | 1.00 |
| | $C_{12}$–$C_{15}$alkylbenzoate | 5.00 |
| | isopropyl palmitate | 5.00 |
| | dimethicone copolyol | 1.00 |
| | stearic acid | 2.00 |
| Phase (B) | deionised water | ad 100 |
| | propylene glycol | 3.00 |
| | carbomer (Carbopol 940, 2% in water) | 8.00 |
| | triethanolamine | 0.70 |

-continued

| | % w/w |
|---|---|
| Phenonip | 0.50 |
| fluorescent whitening agent of formula (103) | 1.00 |

Phase (B) is heated to 80° C. and maintained at that temperature for 20 min. with stirring.
Phase (A), likewise heated to 80° C., is added thereto with stirring and the batch is subsequently stirred for 10 min., cooled to 40° C. and intensively homogenised. The batch is then allowed to cool to room temperature.

What is claimed is:

1. A method of lightening human skin and of protecting human skin against UV radiation, which comprises contacting the skin with a polymeric carrier material selected from the group consisting of starch, starch derivatives, polyvinylpyrrolidones, polyvinylpyrrolidones, polyacrylates, acrylates/steareth-20, methacrylate copolymers, acrylate copolymers, acrylate-octyloropenamide copolymers, acrylate/vinyl isodecanoate cross polymers, $C_1$–$C_{18}$polycarbamylpolyglycol esters, acrylate/hydroxy ester acrylate copolymers, acrylate-octylacrylamides, polyacrylamides, polyamides, polyvinylcaprolactams, polyvinyl alcohols, polyolefin dispersions, polyesters, sodium polystyrenesulfonates, latex particies of all kinds of polymers and copolymers, chitosan and derivatives, xanthans, Gellan, hyaluronic acid, cellulose, cellulose ethers, polyglucans, carboxymethyl-glucans, alginates, hydroxyethyl cellulose, hydroxpropyl cellulose, cyclodextrins (α-, β-, γ-) and their derivatives, polyoxyethylene-polyoxyethylene block polymers, hydrolysed collagen, (hydrolysed) elastin, (hydrolysed) keratin, collagen, gelatin, gum arabic and polyquaternium-X (1–10) treated with a fluorescent whitening agent.

2. A method according to claim 1, wherein the polymeric carrier material comprises (a) an oil-soluble or water-soluble fluorescent whitening agent;

(b) a polymeric compound according to claim 1 and (c) optionally, a solvent.

3. A method according to claim 1, which comprises using as fluorescent whitening agent a compound of formula

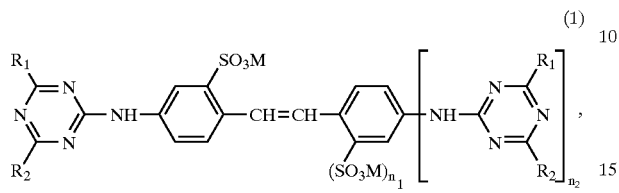

(1)

wherein $R_1$ is a radical of formula

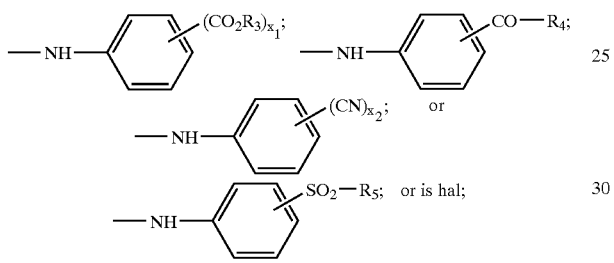

$R_3$ is M; or unsubstituted or substituted alkyl or unsubstituted or substituted aryl;

$R_4$ is hydrogen; unsubstituted or substituted alkyl or unsubstituted or substituted aryl; or —$NR_6R_7$, wherein $R_6$ and $R_7$ are each independently of the other hydrogen; unsubstituted or substituted alkyl or unsubstituted or substituted aryl; or $R_6$ and $R_7$ together with the nitrogen atom binding them form a heterocyclic radical, $R_5$ is hydrogen; unsubstituted or substituted alkyl or unsubstituted or substituted aryl; or a radical of formula (1a) —$(CH_2)_{x_2}$—O—$SO_3$—M;

$R_2$ is hydrogen; unsubstituted or substituted alkyl or unsubstituted or substituted aryl; or a radical of formula

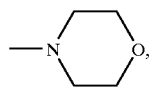

—OH; —$NH_2$; —$N(CH_2CH_2OH)_2$; —$N[CH_2CH(OH)CH_3]_2$; —NH—$R_3$; —$N(R_3)_2$ or —$OR_3$; or $R_1$ and $R_2$ are each independently of the other —OH, —Cl; —$NH_2$, —O—$C_1$–$C_4$alkyl, —O-aryl, —NH—$C_1$–$C_4$alkyl, —$N(C_1$–$C_4$alkyl$)_2$, —$N(C_1$–$C_4$alkyl)(hydroxy-$C_1$–$C_4$alkyl), —$N$(hydroxy-$C_1$–$C_4$alkyl$)_2$; —NH-aryl, morpholino; or S—$C_1$–$C_4$alkyl(aryl);

$R_8$ and $R_9$ are each independently of the other hydrogen, $C_1$–$C_4$alkyl, phenyl or a radical of formula

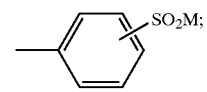

$R_{10}$ is hydrogen, Cl or $SO_3M$;

$R_{11}$ is —CN, —$SO_3M$, —$S(C_1$–$C_4$alkyl$)_2$ or $S(aryl)_2$;

$R_{12}$ is hydrogen, —$SO_3M$, —O—$C_1$–$C_4$alkyl, —CN, —Cl, —COO—$C_1$–$C_4$alkyl or $CON(C_1$–$C_4$alkyl$)_2$;

$R_{13}$ is hydrogen; —$C_1$–$C_4$alkyl, —Cl or —$SO_3M$;

$R_{14}$ and $R_{15}$ are each independently of the other hydrogen, $C_1$–$C_4$alkyl, —$SO_3M$, —Cl or —O—$C_1$–$C_4$alkyl;

$R_{16}$ is hydrogen or $C_1$–$C_4$alkyl;

$R_{17}$ is hydrogen, $C_1$–$C_4$alkyl, —CN, —Cl, —COO—$C_1$–$C_4$alkyl, —$CON(C_1$–$C_4$alkyl$)_2$, aryl or —O-aryl;

M is hydrogen, Na, K, Ca, Mg, ammonium, mono-, di-, tri- or tetra-$C_1$–$C_4$alkylammonium, mono-, di- or tri-$C_1$–$C_4$hydroxyalkylammonium, or ammonium di- or tri-substituted by a mixture of $C_1$–$C_4$alkyl and $C_1$–$C_4$hydroxyalkyl groups;

$n_1$, $n_2$ and $n_3$ are each independently of the others 0 or 1;

$x_1$ is 1 or 2; and $x_2$ is from 1 to 3.

4. A method according to claim 1, which comprises using as fluorescent whitening agent a compound of formula

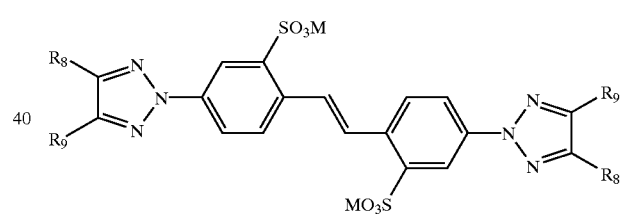

(2)

wherein $R_8$ and $R_9$ are each independently of the other hydrogen; $C_1$–$C_4$alkyl; phenyl; or a radical of formula

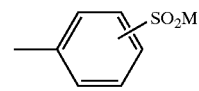

in which

M is hydrogen, Na, K, Ca, Mg, ammonium, mono-, di-, tri- or tetra-$C_1$–$C_4$alkylammonium, mono-, di- or tri-$C_1$–$C_4$hydroxyalkylammonium, or ammonium di- or tri-substituted by a mixture of $C_1$–$C_4$alkyl and $C_1$–$C_4$hydroxyalkyl groups.

5. A method according to claim 1, which comprises using as fluorescent whitening agent a compound of formula (3)

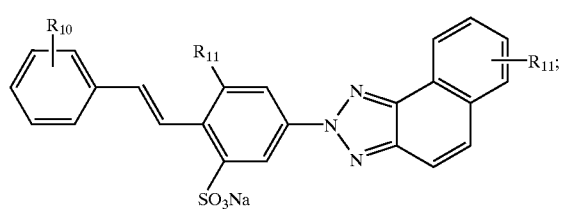

wherein $R_{10}$ is hydrogen, Cl or $SO_3M$;

$R_{11}$ is —ON, —$SO_3M$, —$S(C_1-C_4alkyl)_2$ or $S(aryl)_2$ and

M is hydrogen, Na, K, Ca, Mg, ammonium, mono-, di-, tri- or tetra-$C_1$–$C_4$alkylammonium, mono-, di- or tri-$C_1$–$C_4$hydroxyalkylammonium, or ammonium di- or tri-substituted by a mixture of $C_1$–$C_4$alkyl and $C_1$–$C_4$hydroxyalkyl groups.

6. A method according to claim 1, which comprises using as fluorescent whitening agent a compound of formula (4)

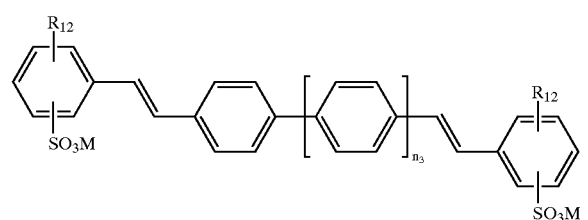

wherein $R_{12}$ is hydrogen, —$SO_3M$, —O—$C_1$–$C_4$alkyl, —CN, —Cl, —COO—$C_1$–$C_4$alkyl or $CON(C_1-C_4alkyl)_2$;

$n_3$ is 0; or 1; and

M is hydrogen, Na, K, Ca, Mg, ammonium, mono-, di-, tri- or tetra-$C_1$–$C_4$alkylammonium, mono-, di- or tri-$C_1$–$C_4$hydroxyalkylammonium, or ammonium di- or tri-substituted by a mixture of $C_1$–$C_4$alkyl and $C_1$–$C_4$hydroxyalkyl groups.

7. A method according to claim 1, which comprises using as fluorescent whitening agent a compound of formula (5)

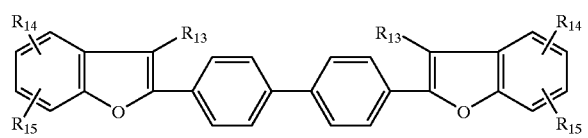

wherein $R_{13}$ is hydrogen; —$C_1$–$C_4$alkyl, —Cl or —$SO_3M$;

$R_{14}$ and $R_{15}$ are each independently of the other hydrogen, $C_1$–$C_4$alkyl, —$SO_3M$, —Cl or —O—$C_1$–$C_4$alkyl; and M is hydrogen, Na, K, Ca, Mg, ammonium, mono-, di-, tri- or tetra-$C_1$–$C_4$alkylammonium, mono-, di- or tri-$C_1$–$C_4$hydroxyalkylammonium, or ammonium di- or tri-substituted by a mixture of $C_1$–$C_4$alkyl and $C_1$–$C_4$hydroxyalkyl groups.

8. A method according to claim 1, which comprises using as fluorescent whitening agent a compound of formula (6)

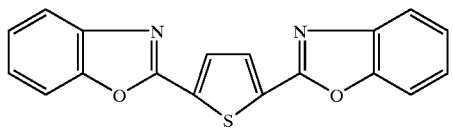

9. A method according to claim 1, which comprises using as fluorescent whitening agent a compound of formula (7)

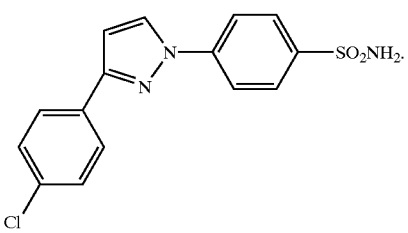

10. A method according to claim 1, which comprises using as fluorescent whitening agent a compound of formula (8)

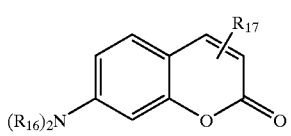

wherein $R_{16}$ is hydrogen or $C_1$–$C_4$alkyl; and $R_{17}$ is hydrogen, $C_1$–$C_4$alkyl, —CN, —Cl, —COO—$C_1$–$C_4$alkyl, —$CON(C_1-C_4alkyl)_2$, aryl or —O-aryl.

11. A method according to claim 1, which comprises using cellulose as polymeric carrier material.

12. A cosmetic formulation, comprising a polymeric carrier material treated with a fluorescent whitening agent according to claim 1, together with at least one UV-protective substance and cosmetically tolerable carriers or adjuvants.

13. A pharmaceutical formulation, comprising a polymeric carrier material treated with a fluorescent whitening agent according to claim 1, together with pharmaceutically tolerable carriers or adjuvants.

14. A method for lightening and for protecting against UV radiation components of cosmetic and pharmaceutical formulations, which comprises incorporating in the formulation a polymeric carrier material treated with a fluorescent whitening agent.

15. A formulation according to claim 13, which comprises in addition UV-protective substances.

* * * * *